United States Patent [19]
Jones et al.

[11] Patent Number: 5,916,967
[45] Date of Patent: Jun. 29, 1999

[54] MIXED SURFACTANT AND HYDROPHOBICALLY-MODIFIED POLYMER COMPOSITIONS

[75] Inventors: Charles Elwood Jones, Yardley, Pa.; Paul Francis David Reeve, Valbonne, France

[73] Assignee: Rohm and Haas Company, Phila. Pa.

[21] Appl. No.: 09/059,067

[22] Filed: Apr. 13, 1998

[30] Foreign Application Priority Data

May 2, 1997 [FR] France .................................. 97 05478

[51] Int. Cl.⁶ ................................ C11D 1/38; C11D 1/86
[52] U.S. Cl. ......................... 524/732; 510/405; 510/417; 510/422; 510/470; 510/473; 510/475
[58] Field of Search ..................... 524/732, 35; 510/405, 510/417, 422, 470, 473, 475

[56] References Cited

U.S. PATENT DOCUMENTS

| | | |
|---|---|---|
| 4,079,028 | 3/1978 | Emmons et al. . |
| 4,384,096 | 5/1983 | Sonnabend . |
| 4,426,485 | 1/1984 | Hoy et al. . |
| 4,496,708 | 1/1985 | Dehm et al. . |
| 4,648,987 | 3/1987 | Smith et al. ............................. 252/559 |
| 5,281,654 | 1/1994 | Eisenhart et al. . |
| 5,292,843 | 3/1994 | Jenkins et al. . |
| 5,425,806 | 6/1995 | Doolan et al. ........................... 106/203 |

FOREIGN PATENT DOCUMENTS

| | | |
|---|---|---|
| WO 98/00494 | 1/1998 | WIPO . |
| WO 98/00495 | 1/1998 | WIPO . |
| WO 98/00499 | 1/1998 | WIPO . |

OTHER PUBLICATIONS

M. Hulden, *Colloids and Surfaces A: Physicochemical and Engineering Aspects*, 82, pp. 263–277 (1996).

C.E. Jones, "A Study of the Interaction of Hydrophobically–Modified Polyols with Surfactants," Proceedings of the 4th World Surfactants Congress, CESIO, Barcelona, 2, pp. 439–450 (1996).

P. Reeve, "Tailoring the Properties of Polymeric Rheology Modifiers to the Characteristics and Requirements of Personal Care Formulations," Proceedings of International Federation of Society of Cosmetic Chemists, IFSCC, Budapest, Apr. 1997.

*Primary Examiner*—Nathan M. Nutter
*Attorney, Agent, or Firm*—Thomas J. Howell

[57] ABSTRACT

Aqueous compositions comprising two or more surfactants and an associative thickener, where the type and amounts of the surfactants are selected to provide an aqueous solution having enhanced thickening properties, is disclosed. In particular, selected surfactant mixtures combined with certain hydrophobically-modified polyetherurethane thickeners provide enhanced thickening properties that are not available when the individual surfactants are combined with thickener. A method for improving the thickening properties of aqueous solutions using the mixed surfactant/associative thickener is also disclosed. The mixed surfactant/associative thickeners of the invention are useful as thickening agents in a variety of formulations such as paints, coatings, cosmetics, personal care items and cleaners.

12 Claims, No Drawings

MIXED SURFACTANT AND HYDROPHOBICALLY-MODIFIED POLYMER COMPOSITIONS

BACKGROUND

This invention relates to aqueous compositions of surfactant mixtures with hydrophobically-modified polymers. In particular, the invention concerns the use of selected surfactant mixtures with hydrophobically-modified polymeric rheology modifiers (thickeners) to provide enhanced thickening efficiency otherwise not available with conventional surfactant/thickener combinations. Compositions of the present invention are useful as thickening agents in a variety of formulations, such as decorative and protective coatings, paper coatings, cosmetics and personal care items, detergents, pharmaceuticals, adhesives and sealants, agricultural formulations, petroleum drilling fluids and cleaners.

Rheology modifiers, or thickeners, have several roles in aqueous systems. They increase viscosity and maintain viscosity at required levels under specified processing conditions and end use situations. In latex decorative coatings, for example, the thickener may provide improved stability, pigment suspension and application properties. In cosmetics and personal care items, the thickener improves body, smoothness and silkiness, making the product more aesthetically pleasing. In petroleum drilling fluids, the thickener improves the suspension of the cuttings, increasing the efficiency with which they can be removed.

Many rheology modifiers, both natural and synthetic, are known. Natural rheology modifiers include, for example, casein, alginates, gum tragacanth, and modified cellulose, including methyl cellulose, hydroxyethyl cellulose, hydroxypropyl cellulose and carbomethoxy cellulose. These natural products vary in their thickening efficiency and generally provide poor flow and leveling properties; they are also subject to microbial attack and require the additional presence of antimicrobial agents. Synthetic rheology modifiers include various acrylic polymers and maleic anhydride copolymers. Some of these are found to be pH dependent, others are hydrolytically unstable, some require large amounts of thickener to effectively increase viscosity, and others are sensitive to various components normally found in aqueous coatings.

A variety of methods have been used to improve the thickening properties of aqueous solutions. For example, the effect of added surfactant on aqueous phase viscosity in the presence of hydrophobically-modified urethane-ethoxylate polymers is disclosed by M. Hulden in *Colloids and Surfaces A: Physicochemical and Engineering Aspects*, 82, pp 263–277 (1996). Similarly, surfactant/thickener interactions are disclosed in "A Study of the Interaction of Hydrophobically-Modified Polyols with Surfactants" by C. E. Jones, Proceedings of the 4th World Surfactants Congress, CESIO, Barcelona, 2, pp 439–450 (1996) and in "Tailoring the Properties of Polymeric Rheology Modifiers to the Characteristics and Requirements of Personal Care Formulations" by P. Reeve, Proceedings of International Federation of Society of Cosmetic Chemists, IFSCC, Budapest, April 1997. Another approach for improving the thickening properties of aqueous solutions using macromonomer-modified polymers as co-thickeners with surfactants is disclosed in U.S. Pat. No. 5,292,843.

The problem addressed by the present invention is to overcome the deficiencies of the prior methods used to increase the viscosity of aqueous systems by providing a thickener composition that can be used at low use levels and in the presence of a wide range of formulation additives (for example, surfactants, salts and pigments) without suffering from compatibility problems.

STATEMENT OF INVENTION

The present invention provides an aqueous composition comprising: (a) a mixed surfactant/associative thickener comprising (i) two or more surfactants selected from nonionic, anionic, cationic and zwitterionic surfactants and (ii) at least one associative thickener selected from one or more of hydrophobically-modified hydroxyethyl cellulose, hydrophobically-modified nonionic polyol and hydrophobically-modified alkali-soluble emulsion polymer; and (b) water; wherein a first surfactant of the two or more surfactants, having a lower calculated HLB value than that of a second surfactant, differs from the second surfactant by at least 1.0 HLB unit; wherein the weight ratio of the first surfactant to the second surfactant is from 30/70 to 99.5/0.5; and wherein the first and second surfactants have a weighted average HLB value of no more than 15.0 HLB units.

The present invention further provides a formulated composition comprising 0.05 to 30 percent by weight, based on weight of the formulated composition, of the mixed surfactant/associative thickener described above, wherein the formulated composition is selected from a paint formulation, a coating formulation, a hair conditioner formulation, a hair shampoo formulation, an astringent formulation, a depilatory formulation, a sunscreen formulation, a facial make-up formulation, a hand cream formulation, a hand lotion formulation, a cleaning formulation, a drilling fluid formulation, a fabric softener formulation, a fabric finishing formulation, an acidic personal care formulation and pesticidal and agricultural formulations.

In another embodiment, the invention provides a method for enhancing thickening efficiency of aqueous compositions comprising combining in an aqueous composition (a) 0.04 to 30 percent by weight of two or more surfactants selected from nonionic, anionic, cationic and zwitterionic surfactants, based on weight of the aqueous composition, and (b) 0.01 to 5 percent by weight of at least one associative thickener selected from one or more of hydrophobically-modified hydroxyethyl cellulose, hydrophobically-modified nonionic polyol and hydrophobically-modified alkali-soluble emulsion polymer, based on weight of the aqueous composition; wherein a first surfactant of the two or more surfactants, having a lower calculated HLB value than that of a second surfactant, differs from the second surfactant by at least 1.0 HLB unit; wherein the weight ratio of the first surfactant to the second surfactant is from 30/70 to 99.5/0.5; and wherein the first and second surfactants have a weighted average HLB value of no more than 15.0 HLB units.

DETAILED DESCRIPTION

We have found that mixtures of two or more surfactants, having specified structural and property differences and combined in selected ratios, may be combined with certain hydrophobically-modified polymeric thickeners in aqueous systems to provide unexpectedly improved viscosity performance when compared to conventional combinations of single surfactants with the hydrophobically-modified polymeric thickeners.

As used herein, all percentages referred to will be expressed in weight percent (%) unless specified otherwise. The phrase "enhanced/enhancing thickening efficiency" means that the observed viscosity (as measured by Brookfield viscometry, for example) of an aqueous system increases by at least about 10%, preferably by at least 25% and more preferably by at least 50%, over that of the aqueous system of a single surfactant with associative thickener being used for comparison. The phrase "(meth) acrylic" means acrylic or methacrylic as it pertains to acid, amide or ester derivatives. As used herein, the phrases "rheology modifier" and "thickener" may be used interchangeably and the phrase "thickener" will be used from hereon. As used herein, the phrase "aqueous composition" means aqueous-based compositions including aqueous solutions and compositions that are substantially aqueous.

Thickeners can be classified by a variety of schemes, for example, according to whether they are synthetic or naturally derived, by the charge on the molecule (anionic, nonionic or cationic), soluble or swellable, and "associative" or "nonassociative." As used herein, the term "associative" thickener is defined as water-soluble or water-swellable polymer that has chemically attached groups that are capable of hydrophobic associations similar to those of conventional surfactants. As used herein, the attached "hydrophobe or hydrophobic group" is any chemical group that promotes water insolubility and includes, for example, alkyl and aralkyl groups containing from about 4 to about 30 carbon atoms. Hydrophobic groups also include, for example, the hydrocarbon residues of hydroxyl, amino or isocyanate reactants (disclosed below) and any portion or segment of the polymeric reaction products (disclosed below) that contributes to water insolubility, including portions or segments other than those of polyether alcohol reactants (disclosed below).

The thickeners of interest in the present invention are of the associative type, for example, (1) naturally derived nonionic thickeners such as hydrophobically-modified hydroxyethyl cellulose (HMHEC), (2) synthetically derived nonionic thickeners such as hydrophobically-modified nonionic polyols (HNP) and (3) synthetically derived anionic thickeners such as hydrophobically-modified alkali-soluble (or swellable) emulsions (HASE).

The associative thickeners can associate with themselves, with surfactants or with other insoluble (hydrophobic) moieties within their environment. The efficiency of the association is controlled by a balance among polymer-polymer interaction, polymer-surfactant and polymer-moiety interactions.

(1) Hydrophobically-Modified Hydroxyethyl Cellulose (HMHEC):

Cellulose derivatives that have been modified with hydrophobic groups such as those described above (alkyl and aralkyl groups containing from 4 to 30 carbon atoms) are useful in the present invention. The hydrophobic groups are typically introduced by well known methods to functionalize some portion of the free hydroxyl groups in the cellulose polymer. An example of a HMHEC is cetyl hydroxyethylcellulose.

(2) Hydrophobically-Modified Nonionic Polyols (HNP):

Polyetherurethanes (or polyalkoxylated urethanes), which are known for use as associative thickeners in latex compositions, are one type of HNP and are condensation polymers of polyether polyols and isocyanates. U.S. Pat. No. 4,079,028 may be consulted for general and specific details concerning types of polyetherurethane thickeners and their preparation.

Generally, the polyetherurethanes are characterized by their end groups. One type of end group is the reaction product of a terminal isocyanate and a polyether alcohol, hereinafter referred to as the "polyether end group." Another type of end group is the reaction product of a terminal isocyanate and a reactant, so that this end group cannot further polymerize or participate in any further reactions once this reaction has occurred, referred to as the "non-functional end group." The end groups of the polyetherurethane may be in any sequence and do not exclude the possibility that the polymer contains additional end groups such as those leading to branched, star-shaped or more complex structures. For any end group that is the reaction product of a polyether alcohol and a terminal isocyanate, the polyether alcohol should have only one terminal hydroxyl moiety that can react with the terminal isocyanate so that the polyether end group cannot further polymerize or react after this reaction has occurred.

The non-functional end group is derived from a reactant that is monofunctional in that it only has one group containing a hydrogen atom that can react with the terminal isocyanate group such as, for example, a monofunctional alcohol, monofunctional amine, monofunctional acid or monofunctional mercaptan.

The polyetherurethanes are prepared in non-aqueous media and are the reaction products of at least reactants (a) and (c), and the polymer may optionally include units corresponding to reactants (b) and (d) shown below:

(a) at least one water-soluble polyether alcohol containing one or more hydroxyl groups,
(b) at least one water-insoluble organic polyisocyanate,
(c) at least one monofunctional hydrophobic organic compound selected from an organic monoisocyanate ($c_1$) and a monofunctional active hydrogen compound ($c_2$), and
(d) at least one polyhydric alcohol or polyhydric alcohol ether.

The polyether alcohol containing one or more functional hydroxyl groups, reactant (a), includes, for example, alkyl and aryl polyether alcohols, and is typically an adduct of an aliphatic, cycloaliphatic, or aromatic polyhydroxy compound such as an adduct of an alkylene oxide and a polyhydric alcohol or polyhydric alcohol ether, a hydroxyl-terminated prepolymer of such adduct and an organic polyisocyanate, or a mixture of such adducts with such prepolymers. Optionally, the polyether alcohol may contain just one hydroxyl group such as an alkyl polyethylene glycol, an alkylaryl polyethylene glycol, or a polycyclic alkyl polyethylene glycol where the alkyl group contains 1 to 20 carbon atoms (straight chain or branched). Suitable alkanol/alkylene oxide and alkylphenol/alkylene oxide adducts, include, for example, methanol, ethanol, propanol, lauryl alcohol, t-octylphenol or nonylphenol/ethylene or propylene oxide adducts containing 1–250 ethylene or propylene oxide groups, such as polyethylene glycol methyl ether and polypropylene glycol methyl ether containing 15–50 alkylene oxide groups.

A convenient source of the hydrophilic polyether polyol adducts is a polyalkylene glycol (also known as a polyoxyalkylene diol) such as polyethylene glycol, polypropylene glycol, or polybutylene glycol, of about 200 to about 20,000 molecular weight. However, adducts of an alkylene oxide and a monofunctional reactant such as a fatty alcohol, a phenol or an amine, or adducts of an alkylene oxide and a difunctional reactant such as an alkanolamine (for example, ethanolamine) are also useful. Such adducts are also known as diol ethers and alkanolamine ethers.

Suitable compounds providing polyether segments also include amino-terminated polyoxyethylenes of the formula $NH_2(CH_2CH_2O)_xH$ where x ranges from about 10 to 200.

Reactant (c), a monofunctional hydrophobic organic compound, reacts with one or both terminal functional groups of the reaction product of reactants (a) and (b) and acts as a "capping" compound for the terminal functional groups of the reaction product. A monofunctional hydrophobic organic compound includes both an organic monoisocyanate (cl) and a monofunctional active hydrogen compound ($c_2$).

The monoisocyanate ($c_1$) may include ($C_6$–$C_{18}$)straight chain, branched chain, and cyclic isocyanates, such as for example, butyl isocyanate, octyl isocyanate, dodecyl isocyanate, octadecyl isocyanate and cyclohexyl isocyanate. These isocyanates may be used singly or in mixtures of two or more thereof.

In addition to an organic monoisocyanate ($c_1$), reactant (c) may be a monofunctional active hydrogen compound ($c_2$). As used herein, the term "monofunctional active hydrogen compound" means an organic compound having only one group which is reactive with isocyanate, such group containing an active hydrogen atom, where any other functional groups, if present, being substantially unreactive to isocyanate. Such compounds include monohydroxy compounds such as alcohols, alcohol ethers and monoamines, as well as polyfunctional compounds providing the compound is only monofunctional to isocyanates. Among the monofunctional active hydrogen compounds useful in the present invention are, for example, the fatty ($C_1$–$C_{40}$)alcohols such as methanol, ethanol, cyclohexanol, octanol, decanol, dodecanol, tetradecanol, hexadecanol (cetyl alcohol), octadecanol (stearyl alcohol) and behenyl alcohol with the ($C_{14}$–$C_{20}$)alkyl alcohols being preferred; phenolics such as phenol, cresol, t-octylphenol, nonylphenol and dodecylphenol; alcohol ethers such as the monomethyl, monoethyl and monobutyl ethers of ethylene glycol, and the analogous ethers of diethylene glycol; alkyl and alkaryl polyether alcohols such as straight or branched ($C_1$–$C_{22}$)alkanol/ ethylene oxide and alkyl phenol/ethylene oxide adducts.

Amino compounds may be used in place of all or a portion of the monohydroxy compounds as hydrophobic monofunctional active hydrogen compounds. Amino compounds include, for example, primary and secondary aliphatic, cycloaliphatic and aromatic amines, such as the straight or branched chain alkyl amines and mixtures thereof, containing about 1 to about 20 carbon atoms in the alkyl group. Suitable amines include, for example, n- and t-octylamine, n-dodecylamines, ($C_{12}$–$C_{14}$) or ($C_{18}$–$C_{20}$)t-alkylamine mixtures, and secondary amines such as N,N-dibenzylamine, N,N-dicyclohexylamine and N,N-diphenylamine. The amino compound may contain more than one active hydrogen atom provided that under normal reaction conditions it is only monofunctional towards an isocyanate group, such as a primary amine.

Monofunctional acids may also be used in place of all or a portion of the monohydroxy compounds and include, for example: ($C_8$–$C_{22}$)alkyl carboxylic acids, such as, for example, octanoic acid, decanoic acid, tetradecanoic acid, hexadecanoic acid, octadecanoic acid (stearic acid), eicosanoic acid and docosanoic acid; naturally occurring mixtures of acids, such as cocoa acids, tallow acids, rapeseed acids and the hydrogenated forms of these acids; aromatic acids, such as benzoic acid and napthenoic acids; alkyl substituted aromatic acids, such as octylbenzoic acid and dodecylbenzoic acid; alicyclic acids, such as cyclopentane carboxylic acid, cyclohexanecarboxylic acid and cyclooctanecarboxylic acid; and alkoxypropyl acids derived from the Michael addition of alcohols of acrylic acid, such as 3-octyloxypropanoic acid, 3-dodecyloxypropanoic acid and 3-octadecyloxypropanoic acid.

Monofunctional mercaptans may also be used in place of all or a portion of the monohydroxy compounds and include ($C_1$–$C_{30}$)alkyl mercaptans, for example: octyl mercaptan, decyl mercaptan, dodecyl mercaptan, tetradecyl mercaptan, hexadecyl mercaptan and octadecyl mercaptan.

The organic polyisocyanate, reactant (b), includes di- and triisocyanates, isocyanate-terminated adducts of such polyhydric alcohols and organic di- or triisocyanates, as well as isocyanate-terminated prepolymers of polyalkylene ether glycols and organic di- or triisocyanates. While it is preferred that reactant (b) be an organic polyisocyanate, reactants containing one or more functional groups other than isocyanate are also suitable. The following are examples of monomers which can be used as reactant (b). These monomers may be used singly or in combination with one or more other reactant (b) monomers: 1,6-hexamethylene diisocyanate (HDI); tolylene 2,4- and 2,6-diisocyanate (TDI); 4,4'-methylene diphenylisocyanate (MDI); 4,4'-biscyclohexylmethane diisocyanate (HMDI); isophorone diisocyanate (IDI); aliphatic triisocyanate product of the hydrolytic trimerization of 1,6-hexamethylene diisocyanate, sold under the brand name Desmodur N.

The polyisocyanates also include any polyfunctional isocyanate derived from reaction of any of the foregoing isocyanates and an active hydrogen compound having a functionality of at least two, such that at least one isocyanate group remains unreacted. Use of such isocyanates is equivalent to chain-extending an isocyanate terminated isocyanate/ diol reaction product with a reactant containing at least two active hydrogen atoms in a manner well known in polyetherurethane synthesis.

The isocyanates may contain any number of carbon atoms effective to provide the required degree of hydrophobic character. Generally, about 4 to 30 carbon atoms are sufficient, the selection depending on the proportion of the other hydrophobic groups and hydrophilic polyether in the product.

Reactant (d), a polyhydric alcohol or polyhydric alcohol ether, may be used to terminate isocyanate functionality or to link isocyanate-terminated reaction intermediates. The polyhydric alcohol or polyhydric alcohol ether may be aliphatic (such as pentaerythritol), cycloaliphatic or aromatic and may be used singly or in mixtures of either type or mixtures of the two types.

By appropriate selection of reactants and reaction conditions, including proportions and molecular weights of reactants, a variety of polymeric products may be obtained that may be linear or complex in structure, such as branched, star-shaped or a mixture of linear, branched and sub-branched materials that form networks of hydrophobes and hydrophobic segments interspersed with hydrophilic segments. In summary, the reaction products formed include, for example, the following:

(i) a reaction product of at least one water-soluble polyether alcohol reactant (a) containing at least one functional hydroxyl group, a water-insoluble organic polyisocyanate reactant (b), and a monofunctional hydrophobic organic compound reactant (c) that is an organic monoisocyanate ($c_1$);

(ii) a reaction product of the water-soluble polyether alcohol reactant (a) and an organic monoisocyanate reactant (cl);

(iii) a reaction product of reactant (a), reactant (b), an organic monoisocyanate reactant ($c_1$) and a polyhydric alcohol or polyhydric alcohol ether reactant (d);

(iv) a reaction product of reactant (a), reactant (b) containing two isocyanate groups, and a monofunctional hydrophobic organic compound reactant (c) that is a monofunctional active hydrogen containing compound ($c_2$); and (v) a reaction product of reactant (a), reactant (b) containing at least three isocyanate groups, and a monofunctional active hydrogen containing compound reactant ($c_2$).

The polymers are prepared according to techniques generally known for the synthesis of urethanes preferably such that no isocyanate remains unreacted. Water should be excluded from the reaction since it will consume isocyanate functionality. If desired, the reaction may be run in a solvent medium in order to reduce viscosity in those reactions leading to higher molecular weight products. Generally, a solvent is useful when molecular weights (number average) of 30,000 or higher are encountered. The solvent should be inert to isocyanate and capable of dissolving the polyoxyalkylene reactant and the urethane product at reaction temperature. Order of addition, reactant proportions and other conditions of reaction such as the selection of the catalyst may be varied to control the geometry, molecular weight and other characteristics of the products, in accordance with well-known principles of polyetherurethane synthesis.

In one embodiment of the invention, the preferred HNP is a mixture of polyetherurethanes containing (a) 5 to 30%, preferably from 8 to 25%, and more preferably from 12 to 25%, of a first polyetherurethane having at least two end groups, where each end group comprises a terminal isocyanate and a polyether; (b) 20 to 80%, preferably from 25 to 75%, and more preferably from 25 to 60%, of a second polyetherurethane having at least two end groups, where each end group comprises a terminal isocyanate group and a non-functional group; and (c) 15 to 60%, preferably from 17 to 50%, and more preferably from 25 to 50%, of a third polyetherurethane having at least two end groups, where one end group comprises a terminal isocyanate and a polyether and one other end group comprises a terminal isocyanate and a non-functional group, where all % are expressed in mole % based on total moles of reactants used.

When the above mixture of polyetherurethanes is used as the thickener component of the mixed surfactant/associative thickener of the present invention, it is preferred that (i) the polyether is selected from an alkyl or aryl polyether alcohol; more preferably the polyether is polyethylene glycol methyl ether (such as polyethylene glycol monomethyl ether having a molecular weight of approximately 550) or polypropylene glycol methyl ether; (ii) the non-functional group is octadecanol (stearyl alcohol); (iii) the polyetherurethane segments are based on polyethylene glycol (molecular weight 8,000) and HMDI; and the molecular weight of the polyetherurethane is approximately 60,000. U.S. Pat. No. 5,281,654 may be consulted for general and specific details, including preparation, concerning HNP based on the polyetherurethane mixtures described above.

U.S. Pat. Nos. 4,426,485 and 4,496,708 may be consulted for general and specific details concerning types of polyetherurethane thickeners having a "comb-like" structure and their preparation. Polyetherurethanes based on polyethylene glycol (molecular weight=8000), polyisocyanates selected from TDI and IDI, and polyhydric alcohols selected from 3-nonylphenoxy-1,2-propanediol and 1,2-hexadecanediol, are preferred.

(3) Hydrophobically-Modified Alkali-Soluble Emulsion Polymers (HASE):

Acrylic carboxylate emulsion polymers are traditionally known for use in a wide variety of thickening applications, including latex coatings, drilling muds and cosmetics. U.S. Pat. No. 4,384,096 may be consulted for general and specific details concerning types of associative acrylic carboxylate emulsion thickeners and their preparation. The acrylic carboxylate emulsion polymers are non-water-soluble, but become soluble in water and thicken when the pH is adjusted from about 5.5 to about 12. The acrylic carboxylate emulsion polymers that are useful in the present invention as associative thickeners are formed from (1) at least one monoethylenically unsaturated carboxylic acid, (2) at least one (meth)acrylic acid ester of an alkoxylated hydrocarbyl or complex hydrophobe alcohol, (3) at least one nonionic ($C_2$–$C_{12}$) monoethylenically unsaturated monomer and optionally (4) one or more polyethylenically unsaturated monomers or chain transfer agents. Specifically, monomers (1), (2), (3), and (4) for forming the associative-type acrylic carboxylate emulsion polymers are described as follows:

(1) A monoethylenically unsaturated carboxylic acid selected from one or more of (meth)acrylic acid, itaconic acid and aryloxypropionic acid; acrylic acid and methacrylic acid are preferred. The carboxylic acid portion of the copolymer may be present in the acid form or neutralized with any common base alkali metal, alkaline earth metal, ammonia, low molecular weight amine or quaternary salt hydroxide to form a water-soluble salt.

(2) A (meth)acrylic acid ester of an alkoxylated ($C_8$–$C_{30}$) alkyl, alkylaryl, polycyclic hydrocarbyl or complex hydrophobe alcohol having at least two oxyalkylene units and as many as 70 oxyalkylene units, preferably having 10 to 40 oxyalkylene units. This ester has the following general formula (I):

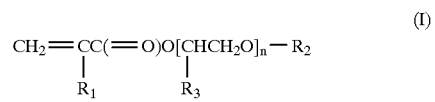

wherein:

$R_1$ is H or $CH_3$, the latter being preferred;

n is from 2 to 70, preferably from 10 to 60, more preferably from 10 to 40;

$R_2$ is a hydrophobic group, for example a ($C_8$–$C_{30}$) alkyl, alkylaryl or polycyclic alkyl group; or a complex branched hydrophobe containing poly(alkylenoxide) branches capped with hydrophobic alkyl or alkylaryl groups as described above; preferably $R_2$ is a ($C_{16}$–$C_{18}$) alkyl or alkylaryl group; and $R_3$ is H or $CH_3$, the former being preferred;

(3) A nonionic ($C_2$–$C_{12}$)monoethylenically unsaturated monomer selected from one or more of ($C_1$–$C_4$)alkyl (meth)acrylate, styrene, acrylonitrile, vinyl choride and vinyl acetate; preferably the monomer is ethyl acrylate, butyl acrylate or methyl methacrylate.

(4) Optionally, a small amount of polyethylenically unsaturated monomer or a chain transfer agent.

A polyethylenically unsaturated monomer, monomer (4), serves to provide molecular weights in the higher range by light crosslinking. Typical monomers used for light crosslinking include diallylphthalate, divinylbenzene, allylmethacrylate and ethylene glycol dimethacrylate. Alternatively, if lower molecular weights are desired, chain transfer agents can be used during the polymerization. Typical monomers useful as chain transfer agents include, for example, carbon tetrachloride, bromoform, bromotrichloromethane, hydroxyethyl mercaptan, β-mercaptopropionic acid; and long chain alkyl mercaptans and thioesters such as n-dodecyl mercaptan, t-dodecyl mercaptan, octyl mercaptan, tetradecyl mercaptan, hexadecyl mercaptan, butyl thioglycolate, isooctyl thioglycolate and dodecyl thioglycolate.

An acrylic carboxylate emulsion of the associative thickener type has a molecular weight (number average) from about 50,000 to about 1,500,000. Preferably, the molecular weight is from 50,000 to 600,000.

For the (meth)acrylic acid ester of an alkoxylated hydrocarbyl alcohol (monomer (2)), $R_2$ may typically be ($C_8$–$C_{24}$) alkyl, an alkylaryl or the residue of a polycyclic hydrocarbyl compound such as lanolin or cholesterol. Alkyl groups include, for example, octyl ($C_8$), lauryl ($C_{12}$), tridecyl ($C_{13}$), myristyl ($C_{14}$), pentadecyl ($C_{15}$), cetyl ($C_{16}$), palmityl ($C_{17}$), stearyl ($C_{18}$), eicosyl ($C_{20}$) and behenyl or docosyl ($C_{22}$). Mixtures may also be used, such as alkyl groups resulting from the alkoxylation of a mixture of lauryl, stearyl, cetyl, and palmityl alcohols. Preferably, the esters are ethoxylated derivatives ($R_3$ of monomer (2) is H). Alkylaryl groups include alkylphenyl groups such as octylphenyl and nonylphenyl. Methods suitable for preparing monomer (2), where the $R_2$ group is a ($C_8$–$C_{30}$) alkyl, alkylaryl or polycyclic alkyl group, are known in the art and are summarized in U.S. Pat. No. 4,384,096. U.S. Pat. No. 5,292,843 may be consulted for general and specific details concerning types of associative acrylic carboxylate emulsion thickeners and their preparation where the $R_2$ group of monomer (2) is a complex branched hydrophobe containing poly (alkylenoxide branches) capped with hydrophobic alkyl or alkylaryl groups.

Monomer components for associative acrylic carboxylate emulsion polymers are used in the ranges of 15 to 60%, and preferably from 20 to 50%, based on weight of monomers used, of the monoethylenically unsaturated carboxylic acid for monomer (1), about 1 to 30%, and preferably from 0.5 to 25%, based on weight of monomers used, of the (meth) acrylic acid ester of an alkoxylated hydrocarbyl or complex hydrophobe alcohol for monomer (2), and 15 to 80%, preferably at least 30%, and more preferably from 40 to 60%, based on weight of monomers used, of the nonionic ($C_2$–$C_{12}$)monoethylenically unsaturated monomer where the monomer is preferably a ($C_1$–$C_4$)alkyl (meth)acrylate for monomer (3). As the optional monomer (4), a chain transfer agent may be used at a level from about 0.1 to 5%, based on weight of monomer, to obtain a low molecular weight; if a high molecular weight polymer is desired, a polyethylenically unsaturated copolymerizable monomer at a level from about 0.05 to 1%, based on weight of monomer, can be used for crosslinking.

Surfactants useful as the surfactant components in the mixed surfactant/associative thickeners of the present invention include nonionic, anionic, cationic, and amphoteric (zwitterionic) surfactants and may be used in combination with each other, the selection depending upon compatibility among the surfactants used and with other ingredients of the thickened aqueous compositions.

Nonionic surfactants are surfactants having no charge when dissolved or dispersed in aqueous solutions. Typical nonionic surfactants useful in the present invention include, for example, ($C_6$–$C_{18}$)alkylphenol alkoxylates (such as t-octyl phenol and nonylphenol ethoxylates having 1–70, and preferably 5–16, ethyleneoxide units), ($C_{12}$–$C_{20}$)alkanol alkoxylates and block copolymers of ethylene oxide and propylene oxide; optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. Useful nonionic surfactants also include, for example, ($C_4$–$C_{18}$)alkyl glucosides as well as the alkoxylated products obtainable therefrom by alkoxylation, particularly those obtainable by reaction of alkyl glucosides with ethylene oxide.

Anionic surfactants are surfactants having a hydrophilic functional group in a negatively charged state in an aqueous solution. Typical anionic surfactants useful in the present invention include, for example, ($C_8$–$C_{18}$)alkyl carboxylic acids, ($C_{12}$–$C_{20}$)sulfonic acids (sulfonated alkylaryl compounds such as sodium dodecylbenzenesulfonate), ($C_{10}$–$C_{20}$)sulfuric acid esters (sulfated alcohols such as lauryl and cetyl sulfates, sodium salts), phosphate esters and salts thereof. Cationic surfactants contain hydrophilic functional groups where the charge of the functional groups is positive when dissolved or dispersed in an aqueous solution. Typical cationic surfactants useful in the present invention include, for example, ($C_{12}$–$C_{20}$)amine compounds (such as lauryl pyridinium chloride, octylbenzyltrimethylammonium chloride and dodecyltrimethylammonium chloride), oxygen containing amines and quaternary amine salts. Amphoteric or zwitterionic surfactants (such as cocamidopropyl betaine) contain both acidic and basic hydrophilic groups and can be used in the present invention.

Generally, nonionic surfactants, such as alcohol ethoxylates are preferred for use in the present invention; however, mixtures of nonionic with anionic, nonionic with cationic, nonionic with amphoteric, anionic with amphoteric, and cationic with amphoteric surfactants may be used as long as they are compatible and satisfy the balance of hydrophilic-lipophilic properties described below.

Typical amounts of the hydrophobically-modified polymeric thickeners used in the mixed surfactant/associative thickener of the present invention are from 0.01 to 5%, preferably from 0.05 to 3% and more preferably from 0.1 to 2%, based on weight of aqueous composition.

Typical combined amounts of the two or more surfactants used in the mixed surfactant/associative thickener of the present invention are from 0.04 to 30%, preferably from 0.01 to 20% and more preferably from 0.5 to 15%, based on weight of aqueous composition.

It is critical that at least two of the surfactants of the aqueous composition differ in their HLB (hydrophilic-lipophilic balance) characteristics by at least 1.0 HLB unit, preferably by at least 2.0 units, more preferably by at least 4.0 units and most preferably by at least 6.0 units. HLB is a value characterizing the relative proportions of hydrophilic and lipophilic portions of molecules, such as the polyetherurethane associative thickeners and the selected surfactants of the present invention; higher HLB values (those approaching 50) represent the more hydrophilic molecules and the lower HLB values (those around 6 to 10) represent the more hydrophobic molecules. HLB values may be calculated or determined by a variety of known procedures, such as those described in "Surfactants and Interfacial Phenomena" by Milton J. Rosen, John Wiley and Son, New York, N.Y., page 244 (1978) and "Interfacial Phenomena" by J. T. Davies and E. K. Rideal, Academic Press, 2nd Edition, pp 373–383 (1963).

The first surfactant of the two or more surfactants is referred to as $S_1$ and has a lower calculated HLB than that of a second surfactant, $S_2$. The magnitude of the difference between $S_1$ and $S_2$ regarding calculated HLB values is indicative of the relative weight ratio of $S_1/S_2$ required to produce the desired enhanced thickening effects in the aqueous compositions of the present invention. In general, the weight ratio of $S_1/S_2$ is from 30/70 to 99.5/0.5, preferably from 40/60 to 97.5/2.5 and more preferably from 50/50 to 95/5. Generally, as the magnitude of the difference in $S_1$ and $S_2$ HLB values increases, the preferred ratio of $S_1/S_2$ increases, that is, a greater amount of the more hydrophobic (lower HLB) surfactant relative to the more hydrophilic (higher HLB) surfactant will provide the best thickening effect.

In addition to the differences in the HLB values of the two or more surfactants and the required ratio of $S_1/S_2$, the overall weighted average HLB value for the $S_1$ and $S_2$ surfactants is an important parameter. Generally, the weighted average HLB value (see formula II):

$$([\text{weight fraction of } S_1] \times [\text{HLB}(S_1)] + [\text{weight fraction of } S_2] \times [\text{HLB}(S_2)]) \quad (II)$$

is 15.0 or less, preferably 13.0 or less and more preferably 12.0 or less, where the weight fraction is based on the combined weights of $S_1$ and $S_2$. For weighted average HLB values greater than about 15, the enhanced thickening effect is believed to be negligible because the overall hydrophilicity of the surfactant combination nullifies any significant hydrophobic interaction between the surfactants and the associative thickener, thus diminishing the macromolecular interaction phenomena believed to be responsible for the enhanced thickening effect of the mixed surfactant/associative thickener.

In general, the ratio of the combined amount of the two or more surfactants, $S_1$ and $S_2$, to the amount of associative thickener in the aqueous compositions of the present invention is from about 0.5/1 to 20/1, preferably from 0.5/1 to 10/1 and more preferably from 1/1 to 5/1.

While not wishing to be bound by theory, we believe that, in the case of the present invention, the selection of surfactants that differ in the aforementioned structural and physical property parameters in the specified ratios produces a disruption of the conventional aqueous network structure formed by interaction of the associative thickener with the hydrophobic portions of the surfactants such that a structural rearrangement of the aqueous network occurs resulting in "enhanced" association of the solvated surfactant-thickener matrix to produce a more stable and durable network throughout the aqueous phase so that the thickening effect is magnified over what is observed with conventional single surfactant/associative thickener combinations.

At the lower overall HLB values for the surfactant mix, resulting from the parameter limitations described above, the associative thickener is believed to be more tightly and deeply bound into the surfactant structures present in the aqueous phase. Additionally, because of the presence of the two or more surfactants with varying HLB values, we believe that the surfactant structures themselves will be altered from their conventional spherical surfactant micelle form having random motion to a more structured and ordered system, where the presence of the associative thickener should further augment the structure, resulting in "enhanced" or increased viscosity of the aqueous solution.

Nonionic surfactants based on alkylphenol polyethyleneoxide, $OP[CH_2CH_2O]_x$—H (see Table 1), were used to provide the mixed surfactant component to be combined with different associative thickeners. Associative thickeners A, B and C are described below, based on reactant descriptions given for the polyetherurethanes described above. Tables 2–5 show the beneficial effect of using the mixed surfactant (each of the surfactants being present in equal amounts, 50/50) together with the different associative thickeners versus using a single surfactant with the associative thickener (the viscosity of OP-9 surfactant is shown in the tables as representative of the viscosity that would be expected for the "individual" surfactant/associative thickener viscosity having a similar average HLB). The mixed surfactants (at 5%) were combined with the associative thickeners (at 1 and 2% levels) in the aqueous solutions tested. The enhanced thickening effects are approximately proportional to the difference in HLB values between the two surfactants used.

| Associative Thickener | React (a) | React (b) | React (c) | React (d) |
|---|---|---|---|---|
| A | PEG 8000 | HMDI | Decanol | |
| B | PEG 8000 | IDI | | NPPD |
| C | PEG 8000/MePEG | HMDI | Octadecanol | |

HMDI 4,4'-Biscyclohexylmethane diisocyanate.
IDI Isophorone diisocyanate
MePEG Polyethylene glycol monomethyl ether, molecular weight = 550.
PEG 8000 Polyethylene glycol, molecular weight = 8000.
NPPD 3-Nonylphenoxy-1,2-propanediol Associative thickeners A, B and C used in the following studies were provided as aqueous solutions, described as follows: associative thickener A provided as a 35% aqueous solution containing 35% propylene glycol cosolvent; associative thickener B provided as a 17% aqueous solution containing 15% butyl carbitol as a cosolvent; associative thickener C provided as a 15% aqueous solution containing 4% enzymatically-modified starch to maintain fluidity.

TABLE 1

| $OP[CH_2CH_2O]_x$—H | x | HLB |
|---|---|---|
| OP-70 | 70 | 18.7 |
| OP-30 | 30 | 17.3 |
| OP-16 | 16 | 15.8 |
| OP-12 | 12.5 | 14.6 |
| OP-9 | 9.5 | 13.5 |
| OP-7 | 7.5 | 12.4 |
| OP-5 | 5 | 10.4 |
| OP-3 | 3 | 7.8 |
| OP-1 | 1 | 3.6 |

OP = t-octylphenol group
x = number of ethyleneoxide units

TABLE 2

| Mixed Surfactant (5%) Assoc Thickener C (1%) | Viscosity mPa-sec | Average HLB | ΔHLB |
|---|---|---|---|
| OP-9 | 8 | 13.5 | — |
| OP-7/OP-12 | 100 | 13.5 | 2.2 |
| OP-5/OP-16 | 192 | 13.1 | 5.4 |
| OP-3/OP-30 | 4308 | 12.6 | 9.5 |
| OP-1/OP-70 | 992 | 11.2 | 15.1 |

TABLE 3

| Mixed Surfactant (5%) Assoc Thickener C (2%) | Viscosity mPa-sec | Average HLB | ΔHLB |
|---|---|---|---|
| OP-9 | 33 | 13.5 | — |
| OP-7/OP-12 | 25 | 13.5 | 2.2 |
| OP-5/OP-16 | 1550 | 13.1 | 5.4 |
| OP-3/OP-30 | 32750 | 12.6 | 9.5 |
| OP-1/OP-70 | 75583 | 11.2 | 15.1 |

TABLE 4

| Mixed Surfactant (5%)<br>Assoc Thickener A (1%) | Viscosity<br>mPa-sec | Average<br>HLB | ΔHLB |
|---|---|---|---|
| OP-9 | 8 | 13.5 | — |
| OP-7/OP-12 | 8 | 13.5 | 2.2 |
| OP-5/OP-16 | 750 | 13.L | 5.4 |
| OP-3/OP-30 | 192 | 12.6 | 9.5 |
| OP-1/OP-70 | 358 | 11.2 | 15.1 |

TABLE 5

| Mixed Surfactant (5%)<br>Assoc Thickener A (2%) | Viscosity<br>mPa-sec | Average<br>HLB | ΔHLB |
|---|---|---|---|
| OP-9 | 225 | 13.5 | — |
| OP-7/OP-12 | 358 | 13.5 | 2.2 |
| OP-5/OP-16 | 2825 | 13.1 | 5.4 |
| OP-3/OP-30 | 1867 | 12.6 | 9.5 |
| OP-1/OP-70 | 2975 | 11.2 | 15.1 |

Table 6 further illustrates the beneficial effect of using mixed surfactants having different HLB characteristics to enhance thickening effects in aqueous systems; this would ultimately allow significantly lower levels of the thickening agents to be used to achieve desired thickening previously achieved by higher levels of conventional thickening agents. The average HLB of the mixed surfactants and the ΔHLB values for the D (single surfactant/associative thickener), E, F, G and H surfactant/associative thickener mixtures in Table 6 were 12.0 and 0, 13.0 and 1.1, 13.1 and 2.2, 13.4 and 4.9, 13.3 and 4.2, respectively. The mixed surfactant/associative thickener systems involving associative thickeners A and B show the most beneficial effect on enhanced viscosity, with the greatest effect shown for the G and H mixed surfactant/associative thickener combinations The mixed surfactant/associative thickener solutions tested for viscosity enhancement were made up by combining 50 parts of solution X (containing the associative thickener C) and 50 parts of solution Y (containing the surfactants): solution X contained 83.3% water, 6.67% of an aqeuous solution of associative thickener C (15%), 1.0% nonyl nonoxynol-40, 4.0% ethanolamine and 5% of a 30% aqueous solution of cocamidopropylbetaine; solution Y contained 80% water and 20% of surfactant R-2, surfactants R-1/R-3 (50/50) and surfactants R-2/R-3 (50/50), respectively. The combined solutions represented 1% of associative thickener C and 10% total surfactant.

The average HLB and the ΔHLB values for the surfactant components of the single surfactant/associative thickener mixture and the mixed surfactant/associative thickener mixtures are shown in Table 7 and again show the beneficial effect of mixed surfactants having different HLB values on solution viscosity when combined with associative thickeners.

TABLE 7

Viscosity Enhancement of Mixed Surfactant/Associative Thickener

| RPM for<br>Viscosity<br>Measurement | C + R-2 | C + R-1/R-3 | C + R-2/R-3 |
|---|---|---|---|
| 6 | 2833 | 5000 | 28000 |
| 10 | 3000 | 3800 | 22400 |
| HLB (aver) | 11.8 | 11.4 | 11.3 |
| ΔHLB | 0 | 1.7 | 1.2 |

Brookfield viscosities (mPa-sec) measured with an RV #6 spindle.

Table 8 shows data on the use of alkylphenol polyethyleneoxide surfactants, OP-5 and OP-7 (see Table 1), with anionic surfactants sodium ($C_{12}$) lauryl sulfate (SLS) and ($C_{16}$) cetyl sulfate (CS) to provide the mixed surfactant components to be used with associative thickeners A, B and

TABLE 6

Viscosity Enhancement of Mixed Surfactant/Associative Thickener Systems

| | Associative Thickener (1%) | | | | | | | | |
|---|---|---|---|---|---|---|---|---|---|
| | A | | | B | | | C | | |
| Mixed Surfactant Concentration | 1% | 5% | 10% | 1% | 5% | 10% | 1% | 5% | 10% |
| OP-7 = 100 (D) | 194 | 118 | 122 | 89 | 40 | 58 | 23 | 25 | 48 |
| OP-7/OP-9 = 50/50 (E) | 235 | 104 | 96 | 70 | 31 | 44 | 16 | 20 | 32 |
| OP-7/OP-12 = 70/30 (F) | 190 | 81 | 91 | 67 | 30 | 15 | 15 | 13 | 8 |
| OP-7/OP-30 = 80/20 (G) | 351 | 376 | 329 | 217 | 109 | 128 | 53 | 40 | 80 |
| OP-5/OP-12 = 30/70 (H) | 292 | 88 | 89 | 172 | 35 | 42 | 17 | 13 | 21 |

Viscosities in mPa-sec (millipascal-seconds) or centipoise

Table 7 shows data on the use of nonionic surfactants based on alkyl polyethyleneoxide, $RO[CH_2CH_2O]_x$—H (see surfactants R-1, R-2 and R-3 below) to provide the mixed surfactant component to be combined with associative thickener C. These data show the effect of changing the hydrophobe portion of the surfactant to enhance interaction with the associative thickener rather than the hydrophilic (alkyleneoxide) portion to cause the difference in HLB values of the mixed surfactants.

Surfactant R-1: R=($C_{12}$–$C_{15}$)alkyl, x=7 having HLB of 12.3

Surfactant R-2: R=($C_{14}$–$C_{15}$)alkyl, x=7 having HLB of 11.8

Surfactant R-3: R=($C_{12}$–$C_{15}$)alkyl, x=3 having HLB of 10.8

C. These data show the effect of mixing anionic and nonionic surfactants to achieve the desired HLB difference in the surfactants required to enhance interaction with the associative thickener. The viscosities of OP-5 with associative thickeners A and B are shown for comparison and are believed to be representative of viscosities of the associative thickeners with any of the single surfactants (anionic or nonionic).

CS=HLB of approximately 20

SLS=HLB of approximately 40

The average HLB and the ΔHLB values for the single surfactant/associative thickener mixture and the mixed surfactant/associative thickener mixtures are shown in Table 8 and again show the beneficial effect of mixed surfactants having different HLB values on solution viscosity when combined with associative thickeners.

TABLE 8

Viscosity Enhancement using Mixed Surfactant (Nonionic/Anionic)/ Associative Thickener Combinations

| Assoc Thickener Mixed Surf | A | | | B | | | C | | |
|---|---|---|---|---|---|---|---|---|---|
| Conc | 1% | 5% | 10% | 1% | 5% | 10% | 1% | 5% | 10% |
| OP-5 (100) | | | | | | | | | |
| HLB (aver) | 10.4 | ===> | | | | | | | |
| ΔHLB | 0.0 | ===> | | | | | | | |
| 6 rpm | — | 17 | 433 | 1883 | 19500 | 883 | | | |
| 12 rpm | 8 | 17 | 292 | 2358 | 11417 | 658 | | | |
| 60 rpm | 32 | 12 | 143 | 1460 | 4967 | 417 | | | |
| OP-5/CS (90/10) | | | | | | | | | |
| HLB (aver) | 11.4 | ===> | | | | | | | |
| ΔHLB | 9.6 | ===> | | | | | | | |
| 6 rpm | | | | 610 | 18500 | >$10^6$ | 220 | 86700 | |
| 12 rpm | | | | 661 | 18000 | >$10^6$ | 276 | >$10^6$ | |
| 60 rpm | | | | 701 | >$10^6$ | >$10^6$ | 317 | >$10^6$ | |
| OP-5/SLS (95/5) | | | | | | | | | |
| HLB (aver) | 11.9 | ===> | | | | | | | |
| ΔHLB | 29.6 | ===> | | | | | | | |
| 6 rpm | 1180 | 67000 | 299 | 151 | 164 | 88,5 | 69,6 | 122 | |
| 12 rpm | 1310 | 43600 | 392 | 927 | 1180 | 733 | 3140 | 3290 | |
| 60 rpm | 1290 | >$10^6$ | 860 | 1860 | 3229 | 700 | 9050 | 15370 | |
| OP-7/SLS (95/5) | | | | | | | | | |
| HLB (aver) | 13.8 | ===> | | | | | | | |
| ΔHLB | 27.6 | ===> | | | | | | | |
| 6 rpm | 180 | 145 | 166 | 190 | 95 | 95 | | | |
| 12 rpm | 200 | 177 | 190 | 212 | 130 | 128 | | | |
| 60 rpm | 216 | 190 | 199 | 210 | 120 | 132 | | | |

Viscosities in mPa-sec

The mixed surfactant/associative thickeners useful in the present invention may be incorporated into different formulated compositions in amounts ranging from 0.05% to 30%, preferably from 0.1% to 20%, more preferably from 0.2% to 10% and most preferably from 0.5 to 5%, based on weight of the particular formulation. The associative thickener component may be mixed into the formulated compositions using conventional mixing equipment such as, for example, high speed dispersers, ball mills, sand mills, pebble mills and paddle mixers. The associative thickeners may be in the form of a dry powder, a premixed aqueous solution or a slurry or a solution in a water-compatible solvent. In this regard a solvent may be selected to prepare the associative thickener so that it may be directly mixed into aqueous compositions; also, the composition may normally contain other known ingredients, such as, for example, pigments, defoamers and preservatives in known combinations and amounts depending on the particular end use. The surfactant components of the mixed surfactant/associative thickener are typically added to the formulations as liquids or liquid solutions.

Typical formulated, compositions that may include the mixed surfactant/associative thickener of the present invention include, for example, paints, coatings, synthetic plaster, cosmetics, personal care items (such as shampoos, hair conditioners, hair dyes, hand lotions, hand creams, sunscreens, facial make-up, astringents, depilatories and antiperspirants), adhesives, sealants, inks, drilling fluids, packer fluids, topical pharmaceuticals, cleaners, fabric softeners, fabric finishes, pesticidal and agricultural compositions, and any aqueous compositions that require thickening. It is understood that limited amounts of various additives and conventional adjuvants may be present as part of the aforementioned formulations as long as they do not alter or significantly affect the performance or properties of the mixed surfactant/associative thickener of the present invention; such additives and adjuvants include, for example, anionic, cationic, nonionic and amphoteric surfactants, proteins, synthetic oils, vegetable or animal oils, silicone oils, waxes, resins, gums, humectants, pigments, acidifying or alkalinizing agents, preservatives, dispersants, thickeners, suspending agents, emollients, ($C_1$–$C_{20}$)alcohol solvents, sunscreen agents and perfumes.

The mixed surfactant/associative thickeners of this invention are particularly useful in latex coating compositions, especially in paints. While useful for increasing the viscosity of an aqueous composition, the mixed surfactant/associative thickeners impart good sag resistance to paint formulations containing the compositions. Aqueous compositions thickened with the mixed surfactant/associative thickeners of this invention are structured and solid-like, characteristic of a gel. The gel structure generated by the mixed surfactant/ associative thickener helps the paint formulation resist the tendency to sag; in addition, compositions with gel structure do not drip easily off a paint brush or paint roller. A further advantage of the mixed surfactant/associative thickener of the present invention is that it is resistant to microbial attack and incorporates easily in other aqueous compositions; the mixed surfactant/associative thickener can also be used as a cothickener with other thickeners to obtain an aqueous composition which does not sag and has a desirable balance of other properties, such as for example, flow and leveling. "Sagging" is the downward movement of a coating on a vertical surface between the time of application and setting, resulting in an uneven coating having a thick bottom edge. The resulting sag is usually restricted to a local area of a vertical surface and may have the characteristic appearance of a draped curtain. Sagging is aesthetically undesirable. In addition, coatings which resist the tendency to sag will not easily drip off a paint brush or a paint roller and will not easily drip off a horizontal surface, such as for example, a ceiling. Paint formulations thickened with the mixed surfactant/associative thickener of this invention resist the tendency to sag.

Coating compositions thickened with the mixed surfactant/associative thickener combinations of this invention also have good flow and leveling propeties. "Leveling" as used herein, refers to the degree to which a coating flows out after application so as to obliterate any surface irregularities, such as for example, brush marks, "orange peel", peaks or craters, that have been produced by the mechanical process of applying a coating. Thus, aqueous coatings thickened with the mixed surfactant/associative thickeners of this invention have a desirable, smooth appearance when dried.

The formulated compositions described below include typical use levels of the mixed surfactant/associative thickeners of the present invention and are not meant to be limiting.

Typical latex coating formulations containing the mixed surfactant/associative thickeners of the present invention also contain added pigments, fillers and extenders such as, for example: titanium dioxide, barium sulfate, calcium carbonate, clays, mica, talc and silica. Typical paint formulations containing the aqueous compositions of the present invention include, for example, the following ingredients: water, methyl carbitol, hydrophilic acrylic dispersant, propylene glycol, defoamer, titanium dioxide, clay, acrylic binder, coalescent, defoamer and mixed surfactant/associative thickener (0.3–2%).

Typical cosmetic and personal care formulations containing the mixed surfactant/associative thickeners of the present invention, include, for example, (a) hair conditioners containing quaternary ammonium salt surfactants (such as dicetyldimethylammonium chloride) and mixed surfactant/associative thickener (1%); (b) dandruff shampoos, astringents and sunscreens containing zinc compounds (such as zinc pyrithione, zinc phenol and zinc oxide, respectively) as active ingredient and mixed surfactant/associative thickener (2%) to maintain the zinc salts in suspension; (c) depilatories containing calcium salts of thioglycolic acid as the active ingredient and mixed surfactant/associative thickener (2%) to prevent the calcium salt from settling out; (d) shampoos containing sodium salts/surfactants (such as cocamidopropyl betaine, sodium lauryl sulfate and polyquaterium-10 (cellulose-2-hydroxyethyl-2-hydroxy-3-[trimethylammonio]propyl ether, chloride)) and mixed surfactant/associative thickener (5–10%) to maintain desired viscosity; (e) facial make-ups (such as eye shadow and face powder) and sunscreens containing pigments (such as clay, silica, calcium carbonate, titanium dioxide and zinc oxide) and mixed surfactant/associative thickener (1%) to provide desirable consistency when applied to the skin; (f) hand creams and hand lotions containing various oils and mixed surfactant/associative thickener (2%) to prevent mineral oil/water separation and to provide desired consistency and feel upon application; and (g) acidic personal care products such as α-hydroxy acids containing cationic surfactants, mild organic acids (such as lactic acid, citric acid, glycolic acid and fruit acids) and mixed surfactant/associative thickener (1–2%).

Typical cleaning formulations containing the mixed surfactant/associative thickeners of the present invention include, for example, metal cleaners, de-scalants, toilet bowl cleaners, household cleaners, automatic dishwash rinse agents, transportation cleaners, metal polishes, dairy cleaners, and liquid abrasive cleaners that contain the following ingredients: acids (5–10% of phosphoric acid, sulfuric acid or citric acid, for example) as the active cleaning agents and mixed surfactant/associative thickeners (2%) that must be compatible with the acidic environment and provide the desired end use viscosities.

We claim:

1. An aqueous composition comprising:
    (a) a mixed surfactant/associative thickener comprising:
        (i) two or more surfactants selected from nonionic, anionic, cationic and zwitterionic surfactants, and
        (ii) at least one associative thickener selected from one or more of hydrophobically-modified hydroxyethyl cellulose, hydrophobically-modified nonionic polyol and hydrophobically-modified alkali-soluble emulsion polymer; and
    (b) water;
wherein a first surfactant of the two or more surfactants, having a lower calculated HLB value than that of a second surfactant, differs from the second surfactant by at least 1.0 HLB unit; wherein the weight ratio of the first surfactant to the second surfactant is from 30/70 to 99.5/0.5; and wherein the first and second surfactants have a weighted average HLB value of no more than 15.0 HLB units.

2. The aqueous composition of claim 1 comprising 0.04 to 30 percent by weight of the two or more surfactants, based on total weight of the aqueous composition.

3. The aqueous composition of claim 1 comprising 0.01 to 5 percent by weight of the associative thickener, based on total weight of the aqueous composition.

4. The aqueous composition of claim 1 wherein first surfactant differs from the second surfactant by at least 4.0 HLB units.

5. The aqueous composition of claim 1 wherein the weight ratio of the first surfactant to the second surfactant is from 50/50 to 95/5.

6. The aqueous composition of claim 1 wherein the weighted average HLB value of the first and second surfactants is no more than 13.0 HLB units.

7. The aqueous composition of claim 1 wherein the hydrophobically-modified nonionic polyol is a polyetherurethane comprising a reaction product selected from one or more of:
    (i) a reaction product of at least one water-soluble polyether alcohol reactant (a) containing at least one functional hydroxyl group, a water-insoluble organic polyisocyanate reactant (b), and a monofunctional hydrophobic organic compound reactant (c) that is an organic monoisocyanate ($c_1$);
    (ii) a reaction product of the water-soluble polyether alcohol reactant (a) and the organic monoisocyanate reactant ($c_1$);
    (iii) a reaction product of reactant (a), reactant (b), the organic monoisocyanate reactant ($c_1$), and a polyhydric alcohol or polyhydric alcohol ether reactant (d);

(iv) a reaction product of reactant (a), reactant (b) containing two isocyanate groups, and a monofunctional hydrophobic organic compound reactant (c) that is a monofunctional active hydrogen containing compound ($c_2$); and (v) a reaction product of reactant (a), reactant (b) containing at least three isocyanate groups, and the monofunctional active hydrogen containing compound reactant ($c_2$).

8. The aqueous composition of claim 7 wherein reactant (a) is polyethyleneglycol, reactant (b) is selected from one or more of tolylene 2,4-diisocyanate and 4,4'-biscyclohexylmethane diisocyanate, and reactant (c) is selected from one or more of octadecanol, decanol and polyethylene glycol monomethyl ether.

9. The aqueous composition of claim 1 wherein the hydrophobically-modified alkali-soluble emulsion polymer comprises an acrylic carboxylate emulsion polymer formed from:

(i) 15 to 60 weight percent, based on weight of the acrylic carboxylate emulsion polymer, of at least one monoethylenically unsaturated carboxylic acid selected from one or more of (meth)acrylic acid, itaconic acid, aryloxypropionic acid and salts thereof;

(ii) 1 to 30 weight percent, based on weight of the acrylic carboxylate emulsion polymer, of at least one (meth) acrylic acid ester of an alkoxylated alkyl, alkylaryl, polycyclic hydrocarbyl or complex hydrophobe alcohol of the formula:

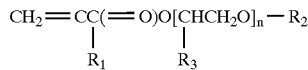

wherein:

$R_1$ is H or $CH_3$;

n is from 2 to 70;

$R_2$ is a hydrophobic ($C_8$–$C_{30}$) alkyl, alkylaryl or polycyclic alkyl group; or a complex branched hydrophobe containing poly(alkylenoxide) branches capped with hydrophobic alkyl or alkylaryl groups as described above;

$R_3$ is H or $CH_3$; and (iii) 15 to 80 weight percent, based on weight of the acrylic carboxylate emulsion polymer, of nonionic ($C_2$–$C_{12}$)monoethylenically unsaturated monomer selected from one or more of ($C_1$–$C_4$)alkyl (meth) acrylate, styrene, acrylonitrile, vinyl choride and vinyl acetate.

10. A formulated composition comprising 0.05 to 30 percent by weight, based on weight of the formulated composition, of the mixed surfactant/associative thickener of claim 1, wherein the formulated composition is selected from a paint formulation, a coating formulation, a hair conditioner formulation, a hair shampoo formulation, a hair dye formulation, an astringent formulation, a depilatory formulation, a sunscreen formulation, a facial make-up formulation, a hand cream formulation, a hand lotion formulation, a cleaning formulation, a drilling fluid formulation, a fabric softener formulation, a fabric finishing formulation, an acidic personal care formulation and pesticidal and agricultural formulations.

11. The formulated composition of claim 10, wherein the cleaning formulation is selected from a metal cleaner, a toilet bowl cleaner, a household cleaner, an automatic dishwash rinse agent, a dairy cleaner and a liquid abrasive cleaner.

12. A method for enhancing thickening efficiency of aqueous compositions comprising combining in an aqueous composition:

a) 0.04 to 30 percent by weight of two or more surfactants selected from nonionic, anionic, cationic and zwitterionic surfactants, based on weight of the aqueous composition, and b) 0.01 to 5 percent by weight of at least one associative thickener selected from one or more of hydrophobically-modified hydroxyethyl cellulose, hydrophobically-modified nonionic polyol and hydrophobically-modified alkali-soluble emulsion polymer, based on weight of the aqueous composition;

wherein a first surfactant of the two or more surfactants, having a lower calculated HLB value than that of a second surfactant, differs from the second surfactant by at least 1.0 HLB unit; wherein the weight ratio of the first surfactant to the second surfactant is from 30/70 to 99.5/0.5; and wherein the first and second surfactants have a weighted average HLB value of no more than 15.0 HLB units.

* * * * *

(12) EX PARTE REEXAMINATION CERTIFICATE (5119th)
United States Patent
Jones et al.

(10) Number: US 5,916,967 C1
(45) Certificate Issued: Jun. 7, 2005

(54) MIXED SURFACTANT AND HYDROPHOBICALLY-MODIFIED POLYMER COMPOSITIONS

(75) Inventors: Charles Elwood Jones, Yardley, PA (US); Paul Francis David Reeve, Valbonne (FR)

(73) Assignee: Rohm and Haas Company, Philadelphia, PA (US)

Reexamination Request:
No. 90/006,345, Aug. 5, 2002

Reexamination Certificate for:
Patent No.: 5,916,967
Issued: Jun. 29, 1999
Appl. No.: 09/059,067
Filed: Apr. 13, 1998

(30) Foreign Application Priority Data

May 2, 1997 (FR) .............................. 97 05478

(51) Int. Cl.⁷ .............................. C11D 1/38; C11D 1/86
(52) U.S. Cl. ..................... 524/732; 510/405; 510/417; 510/422; 510/470; 510/473; 510/475
(58) Field of Search .................. 524/732, 35; 510/405, 510/417, 422, 470, 473, 475

(56) References Cited

U.S. PATENT DOCUMENTS

| 4,177,177 A | * | 12/1979 | Vanderhoff et al. .... 260/29.2 M |
| 4,180,491 A | | 12/1979 | Kim et al. |
| 5,246,503 A | * | 9/1993 | Minick ........................ 134/38 |
| 5,393,454 A | | 2/1995 | Mondin et al. |
| 5,652,208 A | | 7/1997 | Sramek |

FOREIGN PATENT DOCUMENTS

| WO | WO 93/24577 | 12/1993 |

* cited by examiner

*Primary Examiner*—James J. Seidleck

(57) ABSTRACT

Aqueous compositions comprising two or more surfactants and an associative thickener, where the type and amounts of the surfactants are selected to provide an aqueous solution having enhanced thickening properties, is disclosed. In particular, selected surfactant mixtures combined with certain hydrophobically-modified polyetherurethane thickeners provide enhanced thickening properties that are not available when the individual surfactants are combined with thickener. A method for improving the thickening properties of aqueous solutions using the mixed surfactant/associative thickener is also disclosed. The mixed surfactant/associative thickeners of the invention are useful as thickening agents in a variety of formulations such as paints, coatings, cosmetics, personal care items and cleaners.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 4 is cancelled.

Claims 1 and 12 are determined to be patentable as amended.

Claims 2, 3 and 5–11, dependent on an amended claim, are determined to be patentable.

1. An aqueous composition comprising:
   (a) a mixed surfactant/associative thickener comprising:
      (i) two or more surfactants selected from nonionic, anionic, cationic and zwitterionic surfactants, and
      (ii) at least one associative thickener selected from one or more of hydrophobically-modified hydroxyethyl cellulose, hydrophobically-modified nonionic polyol and hydrophobically-modified alkali-soluble emulsion polymer; and
   (b) water;
   wherein a first surfactant of the two or more surfactants, having a lower calculated HLB value than that of a second surfactant, differs from the second surfactant by at least [1.0 HLB unit] *4.0 HLB units*; wherein the weight ratio of the first surfactant to the second surfactant is from 30/70 to 99.5/0.5; and wherein the first and second surfactants have a weighted average HLB value of no more than 15.0 HLB units.

12. A method for enhancing thickening efficiency of aqueous compositions comprising combining in an aqueous composition:
   a) 0.04 to 30 percent by weight of two or more surfactants selected from nonionic, anionic, cationic and zwitterionic surfactants, based on weight of the aqueous composition, and
   b) 0.01 to 5 percent by weight of at least one associative thickener selected from one or more of hydrophobically-modified hydroxyethyl cellulose, hydrophobically-modified nonionic polyol and hydrophobically-modified alkali-soluble emulsion polymer, based on weight of the aqueous composition;
   wherein a first surfactant of the two or more surfactants, having a lower calculated HLB value than that of a second surfactant, differs from the second surfactant by at least [1.0 HLB unit] *4.0 HLB units*; wherein the weight ratio of the first surfactant to the second surfactant is from 30/70 to 99.5/0.5; and wherein the first and second surfactants have a weighted average HLB value of no more than 15.0 HLB units.

\* \* \* \* \*